United States Patent
Pauker

(10) Patent No.: US 6,616,600 B2
(45) Date of Patent: Sep. 9, 2003

(54) ENDOSCOPE SHAFT

(76) Inventor: Fritz Pauker, Kirchberg 2, D-86438 Kissing (DE)

( * ) Notice: Subject to any disclaimer, the term of this patent is extended or adjusted under 35 U.S.C. 154(b) by 0 days.

(21) Appl. No.: 09/801,568

(22) Filed: Mar. 7, 2001

(65) Prior Publication Data

US 2002/0055668 A1 May 9, 2002

Related U.S. Application Data

(63) Continuation-in-part of application No. 09/095,857, filed on Jun. 11, 1998, now Pat. No. 6,286,555, and a continuation-in-part of application No. 09/305,850, filed on May 5, 1999, now Pat. No. 6,358,199.

(51) Int. Cl.$^7$ ............................ A61B 1/005; A61B 25/00
(52) U.S. Cl. ...................... 600/128; 600/139; 600/144; 600/146; 600/153
(58) Field of Search .................. 600/139, 140, 600/144, 146, 152, 121, 123, 128, 153, 156; 604/264, 523

(56) References Cited

U.S. PATENT DOCUMENTS

| | | | | |
|---|---|---|---|---|
| 4,616,631 A | * | 10/1986 | Takahashi | 600/139 |
| 4,976,191 A | * | 12/1990 | Suzumori et al. | 92/103 R |
| 5,860,914 A | * | 1/1999 | Chiba et al. | 600/139 |
| 5,944,654 A | * | 8/1999 | Crawford | 600/157 |

FOREIGN PATENT DOCUMENTS

DE    42 42 291 A1    6/1994

* cited by examiner

*Primary Examiner*—John Mulcahy
(74) *Attorney, Agent, or Firm*—Graybeal Jackson Haley LLP

(57) ABSTRACT

The invention relates to an endoscope shaft comprising a hose body which forms a central working conduit and a number of functional conduits. According to the invention, the hose body is manufactured of an extruded synthetic material surrounded by a silicone clothing or cover which forms the outer layer of the endoscope shaft.

13 Claims, 2 Drawing Sheets

Figure 4:
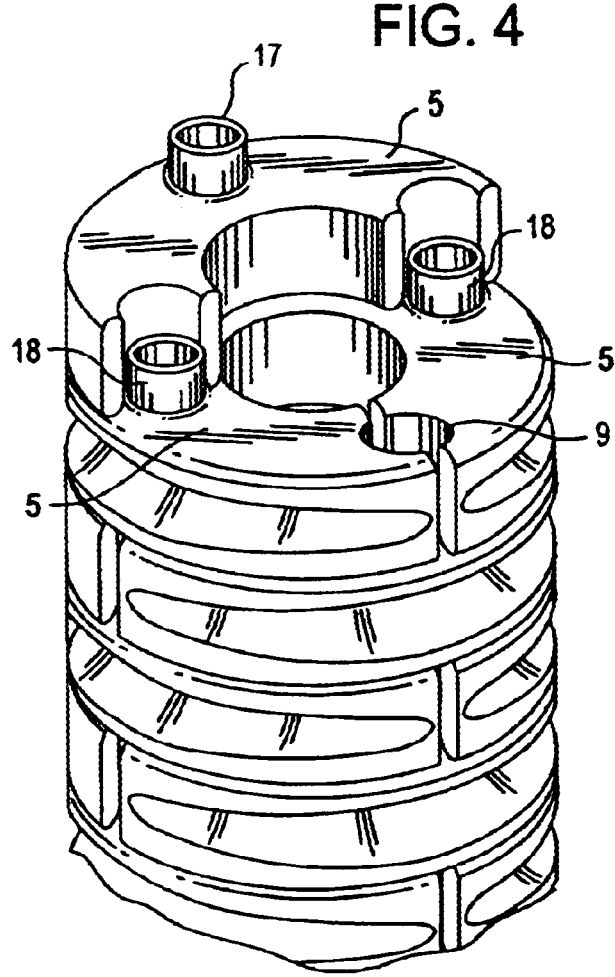

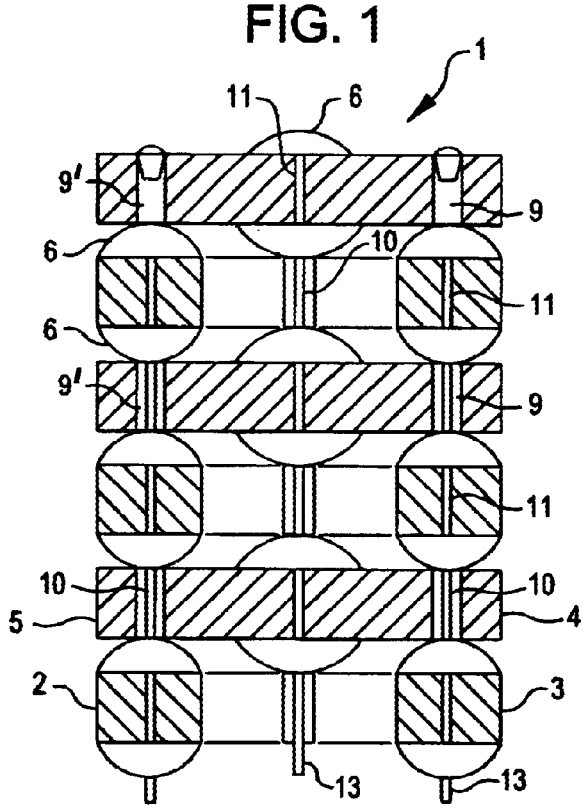
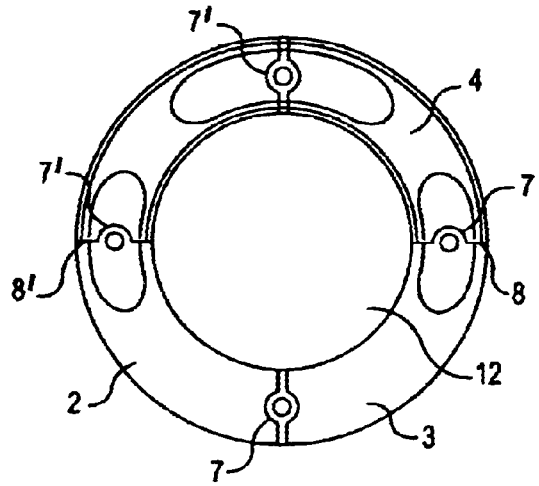
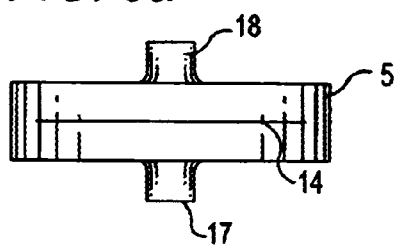
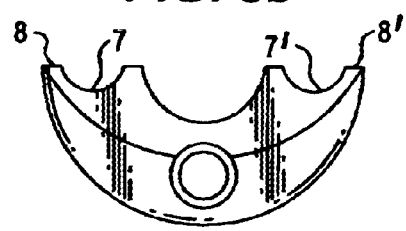
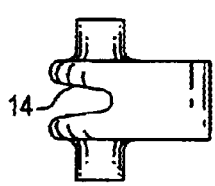
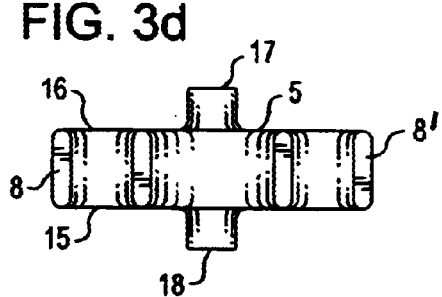

ENDOSCOPE SHAFT

This is a continuation-in-part of application Ser. No. 09/095,857 filed on Jun. 11, 1998 now U.S. Pat. No. 6,286,555, and continuation-in-part of U.S. application Ser. No. 09/305,850 filed on May 5, 1999 now U.S. Pat. No. 6,358,199.

The present invention relates to an endoscope shaft in accordance with the preamble of claim 1.

Endoscopes are instruments especially for exploring hollows or tube-shaped conduits of the body, for instance for medical purposes. Endoscopes of this kind are preferably used for exploring the esophagus, the stomach, the duodenum from the stomach, the intestine from the anus, the urethra, the vesica and the ureter. Endoscopes are mostly equipped with a lighting device at their front end and with an optical system for visually detecting the area of the body hollow or body canal located forward thereof.

Further endoscopes usually comprise a working conduit or channel as it is called through which various working instruments can be introduced and operated, e.g. forceps for taking tissue specimens, biopsy needles, heated cutting wires, small scissors or the like. Finally, as a rule functional conduits, for instance a fluid conduit for wash and operating wires for bending the front end of the endoscope in various directions are provided. Altogether the endoscope has, apart from its rear operating end and a connecting rope, an elongated flexible bar shape. The common outer diameters approximately range from 9 to 15 mm and are somewhat more at the front head.

So far endoscopes have been introduced into the body in that the physician pushes the pressure-stiff endoscope and/or the pressure-stiff endoscope shaft into the body from the part of the endoscope protruding from the body. This way of introducing the endoscope is particularly difficult and time-consuming especially in the case of the coloscope, as in the latter case the intestine has bends and frequently isthmuses. Accordingly, coloscopic examinations have been costly examinations which are unpleasant to the patient so far and therefore are hardly taken into account for a wide-spread application. Moreover the handling of a coloscope requires a physician experienced in this matter.

Furthermore the prior art has shown that endoscopes of the known construction represent extremely complicated and thus cost-intensive designs due to the stiffness required for inserting them into the patient's hollow to be examined and at the same time the necessary flexibility. These constructions are so expensive that they have to be employed again and again. Therefore it is necessary to take costly sterilizing measures after each examination, wherein there is finally also a risk of damaging the endoscope shaft, especially when such sterilizing operations are carried out by an untrained staff.

In view of this situation, it is the object of the invention to provide an endoscope shaft which can be manufactured in a considerably less expensive way and in which the risk of damaging, for instance during sterilizing operations, is eliminated.

This object of the invention is achieved by an endoscope shaft comprising the features of claim 1.

The invention is based on the following consideration:

An endoscope of this species is known from prior art, especially according to DE 42 42 291 A1. This endoscope substantially consists of an endoscope head, or a distal end, to which an endoscope shaft made of a flexible yet push-stiff tubular body is connected and an operating device at the lower end of the endoscope shaft. The operating device includes a number of actuating wheels rotatably mounted on the endoscope shaft which are operatively connected with the distal end through operating wires or Bowden wires movably laid within the endoscope shaft.

For introducing this endoscope shaft into the intestine of a patient to be treated, for instance, this prior art makes use of a kind of double reversing hose system, as it will be briefly described hereinafter:

The double reversing hose system known from this publication provides to slidingly guide the endoscope shaft in a two-sided reversed hose which in turn is movable by a drive means acting on the inner hose portion of the reversing hose which is formed hereby. The drive means includes at least a continuously driving feed means, for instance a number of drive wheels, which can be radially forced onto the inner hose portion to move the latter substantially continuously in axial direction of the shaft. This has the advantage that the continuous advance of the reversing hose system can be exactly controlled and thus the distal end of the endoscope, for example, can be guided exactly to the point.

Here it is provided that the pressing force of the feed means acting on the inner hose portion is selected so that the shaft is in direct frictional contact with the inner hose portion at least in the area of the feed means. The feed means is constituted by one or more frictional wheels, as already indicated in the foregoing, which can be biased against the inner hose portion at a predetermined or adjustable pressing force so that a continuous and as slip-free as possible feed of the endoscope shaft into a patient's hollow is ensured. The endoscope shaft itself forms the abutment of the frictional wheels.

Moreover the drive means includes a device for synchronizing the movement of the shaft with the movement of the reversing hose. This may be a rear and front end or clamping piece axially fixed to the shaft to which the rear or front reversing portion of the reversing hose depending on the direction of feed is glidingly adjacent so that the reversing hose applies a braking force to the shaft via the rear or front end piece inversely to the currently prevailing feed force. Alternatively to that, the synchronizing device can be a roller or spindle drive acting on the rear end portion of the shaft which is synchronized with the reversing hose drive such that the rate of feed of the shaft is half of the rate of feed of the inner hose portion.

The substantial advantage of the endoscopic apparatus known from DE 42 42 291 A1 consists in the fact that the endoscope shaft is cased over the total length thereof except the front movable distal end portion by the drive means, i.e. the double reversing hose system, and thus does not directly contact the wall of the hollow space. Moreover the double reversing hose system creates a kind of self-propelling, whereby no more feed forces have to be applied to the endoscope shaft from the operating end thereof.

Hence DE 42 42 291 A1 and the technical teaching given there establishes the precondition for forming novel endoscope shafts as they are now the subject matter of the invention.

Consequently, it is the gist of the invention according to claim 1 to provide the endoscope shaft consisting of a hose body which forms a central working conduit and a number of functional conduits with a silicone shell which coats the outside of the above-characterized hose body and thus forms the outer layer of the endoscope shaft. The hose body itself constituting the core of the endoscope shaft consists of an extruded synthetic material.

It has turned out that this structure can be manufactured at especially low costs, because no flexural strengths in the longitudinal direction of the shaft have to be taken into account when employing such a shaft with a drive means in the form of a double reversing hose system of the known design, for instance. Extruded plastic sections are extremely inexpensive, wherein the silicone shell can simply be cast around the extruded hose body.

This structure can be manufactured so inexpensively that the endoscope shaft according to the invention can be used as a disposable rendering sterilizing measures superfluous.

Moreover the silicone shell acts like a soft cushion protecting the hose body against damage in the case of impact. It has further turned out that the silicone shell is suited, despite its highly elastic soft characteristic, as an abutment for a drive means known from prior art, for instance the above-described reversing hose drive system.

Further advantageous embodiments of the invention are the subject matter of the other subclaims.

Hereinafter the invention will be explained in detail by way of a preferred embodiment with reference to the accompanying drawings, in which FIG. 1 shows a schematic representation of a distal end portion of an endoscope shaft in accordance with a preferred embodiment of the invention in a cross-sectional view.

Figure 5:
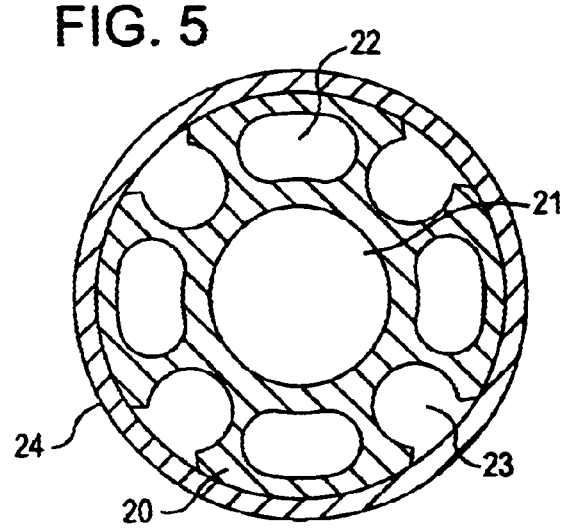

FIG. 2 shows a top view of the distal end portion as a schematic representation, FIGS. 3a to 3d show the structure of a swelling body, FIG. 4 shows the combination of a plurality of swelling bodies in a perspective view forming the distal end in accordance with the preferred embodiment and FIG. 5 is the top view of an endoscope shaft according to the preferred embodiment of the invention.

In FIG. 1 the movable distal end portion of an endoscope shaft according to the preferred embodiment of the invention is shown as a schematic drawing.

As one can take from FIG. 1, the movable distal end portion 1 of the endoscope shaft according to the invention comprises a plurality of bodies 2, 3, 4 longitudinally juxtaposed and/or stacked, each layer being formed of two bodies arranged diametrically with respect to each other.

FIG. 2 shows the top view of the movable distal end portion 1 as a schematic representation. Accordingly, each body 2, 3, 4 consists of a semicircular disc-like ring element 5 forming swelling bodies 6 in its central portion seen in the circumferential direction. At the two respective end faces of the semicircular ring disc 5 notches 7, 7' extending in the direction of thickness of the disc 5 are formed preferably in semicircular shape. The semicircular ring discs 5 are arranged adjacent to each other in each layer at the two end faces 8, 8' thereof such that the opposed notches 7,7; 7',7' define two diametrically opposed through holes 9, 9' at the respective end faces.

As one can further take from FIG. 1, the pairs of bodies which are directly adjacent in the longitudinal direction of the distal end portion are additionally phase-shifted by 90°. Hereby the swelling bodies 6 are alternately arranged at three and nine o'clock with respect to the one layer and to twelve and six o'clock on the respectively neighboring layer.

According to the present embodiment, the swelling bodies 6 are formed as extendable bellows which can be operated pneumatically or hydraulically. As an alternative, it is also possible, of course, to form the swelling bodies 6 as piezoelectric elements.

The swelling bodies 6, in the present case the expandable bellows, form a swivel and/or bend-off mechanism of the movable distal end. To this end, all bellows having the same angular position, i.e. the bellows in the twelve o'clock position, in the three-o'clock position, in the six-o'clock position and in the nine-o'clock position are coupled with each other. This coupling consists of a piece of duct 10 which connects two longitudinally spaced bellows having the same angular position both mechanically and hydraulically and/or pneumatically, these pieces of ducts 10 extending through the through holes 9, 9' of the pair of bodies mounted therebetween. Consequently, a hydraulic and/or pneumatic fluid communication as well as a mechanical coupling is produced by the pieces of ducts 10 for preventing the individual layers from falling apart.

According to FIG. 1, the bellows are principally provided at the opposed flat sides of the semicircular ring discs 5 and have a fluid connection with each other by through bores 11 through which the ring discs 5 are extending.

As one can see from FIG. 2, for each layer a central through hole 12 extending along the entire movable distal end portion 1 and forming a working conduit for introducing surgical instruments, auxiliary instruments or optical equipment is formed by juxtaposing the semicircular ring discs 5 according to the invention.

The function principle of the movable distal end portion according to the invention can be summarized as follows:

If a pressure medium, for instance a hydraulic fluid, is pumped into the fluid-coupled bellows through the pieces of duct 10 in a selected angular position, this causes the bellows to widen substantially in a longitudinal direction of the distal end portion 1, whereby the semicircular ring discs 5 are spaced apart from each other in the area of this angular position. As no pressure is applied to and/or the pressure is even relieved from all further bellows in the respective other angular positions, this causes each layer consisting of two ring discs 5 to tip, whereby the distal end portion is gradually bending over the entire longitudinal extension thereof. The more hydraulic fluid is pressed into the just pressurized bellows, the larger becomes the degree of curvature of the end portion so far that an bend-off of almost 160° can be attained.

Such a bending motion in a direction of movement can be superimposed, of course, by pressurizing bellows in a different angular position, for instance in an angular position offset by 90° hereto, whereby a kind of tumbling motion of the distal end portion is resulting. It is also possible to apply pressure to or to relieve pressure from all bellows in all angular positions so as to longitudinally displace or contract the distal end portion in the area of the total possible expansion of all bellows longitudinally spaced apart from each other.

As soon as the distal end of the movable end portion has adopted a particular bending position, the pressurization of the respective bellows of one or plural angular position(s) is stopped, whereby the distal end portion is fixedly maintained in this bending position due to the incompressible property of the hydraulic fluid.

This fixing is dependent on the elasticity in a radial direction of the bellows themselves, wherein concerning the design of each semicircular ring disc a good elasticity in the longitudinal direction but an as stiff configuration as possible in the radial direction is strived for, as it will be described hereinafter by way of a concrete design.

As one can further take from FIG. 1, the semicircular ring discs 5 of the bottom layer according to FIG. 1 include connecting sleeves 13 for connecting a hydraulic pipe system. This hydraulic pipe system not shown in the present Figures substantially comprises four conduits which are guided through the endoscope shaft, which is not shown either, in working conduits formed therein and are connected to a central hydraulic pressure source. As a hydraulic pressure source preferably a manually operable pressure pump is suited which consists of four individual pumps which are operable independently of each other or coupled in such a manner that when pressure is applied to the bellows of one angular position the pressure is relieved in the bellows in the opposed angular position. Due to such a reciprocal relation between the application of pressure and a pressure relief in respectively opposed rows of bellows, the mobility of the distal end portion can be further increased and the positioning capability can be improved.

The latter even permits the exploration e.g. of the intestine wall in the area of the sphincter muscle from the side of the intestine.

In the FIGS. 3a to 3d the design of a semicircular ring disc 5 is shown in great detail. As one can take herefrom, the ring disc 5 consists of a synthetic body having a predetermined thickness which forms a hollow space. The wall of the body is inwardly folded at least once at the radially outer side so as to form a bellow 14.

At the mutually opposing side faces 15, 16 of the ring disc 5 connecting sleeves 17, 18 are formed which are arranged in alignment and open into the hollow of the ring body 5. The connecting sleeves 17, 18 can be formed integrally with the ring disc 5 or can be welded thereto. The ring body 5 preferably consists of two halves of a shell which are welded to each other along the radially outer side and the radially inner side in a circumferential direction.

Semicircular notches 7, 7' are formed at both end faces 8, 8' of the semicircular ring disc 5 in the direction of thickness of the ring disc 5.

In FIG. 4 the movable distal end portion is structurally shown.

As one can see herefrom, two of the above-described ring discs 5 at a time juxtaposed at their respective end faces 8, 8' form a layer, wherein the pairs of ring discs of each layer which are arranged directly adjacent to each other are phase-shifted by 90°. In order to fix the ring discs 5 which are located at an angular position seen in the longitudinal direction, the connecting sleeves 17, 18 extending through the through holes 9, 9' which are formed in the one layer by the notches 7, 7' formed at the end face are glued or welded to each other. Hereby the above-mentioned piece of duct 10 as well as the mechanical connection of the coupled ring discs 5 in the longitudinal direction are brought about.

Alternatively to the above-mentioned synthetic material design, also rubber or rubber laminate can, of course, be the material used for the distal end portion 1. The distal end portion is welded onto the end front face of the endoscope shaft such that in the two bottom layers the free connecting sleeves 13 make a fluid connection with the hydraulic conduits along the hydraulic shaft.

As represented in FIG. 5, the endoscope shaft includes a hose body 20 made of an extruded synthetic section forming a central working conduit 21 having a large diameter. The working conduit 21 has a through-going connection to the central through hole 12 of the distal end portion 1, as already indicated in the foregoing.

Around the working conduit 21 a number of functional conduits 22 having a smaller cross-section which are radially spaced apart from the central working conduit 21 and are arranged at an equal angular distance from each other are formed in the hose body 20. In the present case, four functional conduits 22 which, as pressure conduits, are in fluid connection with the connecting sleeves to operate the distal end portion 1 are provided in the hose body 20.

At the rear end portion of the endoscope shaft there is provided the pressure medium source which is likewise connected to the functional conduits used as pressure conduits and preferably forms a unity with the endoscope shaft.

A silicone clothing or silicone cover 24 surrounding the hose body 20 substantially over the entire length thereof and preferably ending at the distal end portion 1 in the area of the fastening point thereof at the endoscope shaft or being sealingly welded with the distal end portion 1 at the front end is arranged around the hose body 20 like a shell.

Circular notches or grooves 23 which extend along the hose body 20 and are arranged at equal angular distances from each other are formed radially between the functional conduits in the case surface of the hose body 20. Preferably the grooves 23 are located exactly between the functional conduits 22 of the hose body 20. The grooves 23 are covered by the silicone clothing in a radially sealing manner and thus form outer functional conduits in which cables are laid, for instance, for connecting a camera chip or a lighting fixture at the distal end portion.

As explained already in the beginning, it is particularly advantageous to design the endoscope shaft as a disposable. Therefore, in order to reduce the manufacturing costs the distal end portion made of synthetic material is simply welded onto the front end of the endoscope shaft, the connecting sleeves 17, 18 being fluid-connected with the pressure conduits 22 of the hose body.

It is finally pointed out in this context that the design of the endoscope shaft can by no means be combined only with the distal end portion according to the invention but also with other shaft ends which have been known before. Nor is the operating device restricted to the described manual pump as a disposable but it could also be a conventional reusable pressure source to which the endoscope shaft can be simply connected. In the latter case connecting points are formed at the rear end of the shaft for the connection of communicating ducts between the pressure source and the functional conduits.

The invention relates to an endoscope shaft comprising a hose body forming a central working conduit and a number of functional conduits. According to the invention, the hose body is manufactured of an extruded synthetic material surrounded by a silicone clothing or cover which constitutes the outer layer of the endoscope shaft.

What is claimed is:

1. An endoscope shaft comprising:
    a hose body made from extruded synthetic material and including a central working conduit, a functional conduit, and a longitudinal groove; and
    a cover surrounding the hose body and forming an outer layer of the shaft.

2. The shaft according to claim 1, wherein the synthetic material is stiffer than the cover.

3. The shaft according to claim 1, wherein the hose body includes at least two functional conduits that are formed solely by the hose body and that are pressure conduits for guiding a compressed medium, wherein each functional conduit longitudinally extends through the entire endoscope shaft and is arranged at an equal angular distance from an adjacent functional conduit around the central working conduit.

4. The shaft of claim 1 wherein the hose body includes at least two longitudinal grooves, each arranged at an equal angular distance from an adjacent longitudinal groove.

5. The shaft according to claim 3, wherein the hose body includes a longitudinal groove arranged circumferentially between each functional conduit.

6. An endoscope shaft system comprising:
    an endoscope shaft including:
        a hose body made from extruded synthetic material and including a central working conduit, a functional conduit, and a longitudinal groove;
        a cover surrounding the hose body and forming an outer layer of the shaft;
    a movable distal end portion connected to the endoscope shaft and including a plurality of longitudinally stacked semicircular disc-like ring elements each including a swelling body, wherein two of said ring elements form a layer with their respective swelling bodies located diametrically opposite each other, and wherein the swelling bodies in each layer of ring elements are phase-shifted 90 degrees relative to the swelling bodies of a longitudinally adjacent layer of ring elements; and an operating device operatively connected through the endoscope shaft to the movable distal end portion for the operation thereof.

7. The shaft system according to claim 6, wherein all swelling bodies located at twelve, at three, at six, and at nine o'clock are longitudinally coupled with each other.

8. The shaft system according to claim 7, wherein the swelling bodies are hydraulically or pneumatically operable bellows.

9. The shaft system according to claim 8, wherein the coupling is both mechanical and hydraulic and/or pneumatic, and wherein at least a piece of duct is provided between two bellows at a time which are coupled to each other and are longitudinally spaced apart, the piece of conduit being fixedly mounted to the bellows.

10. The shaft system according to claim 9, wherein the swelling bodies of each layer interact to form a central through hole.

11. The shaft system according to claim 10, wherein the swelling body forms a hollow and is folded at its radial outside.

12. The shaft system according to claim 11, wherein the swelling body is provided at its two front faces with connecting sleeves opening into the hollow and being connected with connecting sleeves of the respective longitudinally spaced swelling bodies at an equal angular position while forming the piece of duct.

13. The shaft system according to claim 12, wherein the swelling body has at its end faces longitudinally extending notches which, upon the formation of a layer, form two diametrically opposite through conduits through each of which a piece of duct is guided.

* * * * *